United States Patent [19]

Hunkin et al.

[11] Patent Number: 4,590,810
[45] Date of Patent: May 27, 1986

[54] LIQUID SAMPLE COLLECTOR AND METHOD FOR OBTAINING SAMPLES

[76] Inventors: Geoffrey G. Hunkin, 9 Meadow Lark La.; Thomas A. Reed, 6458 S. Garland Ct., both of Littleton, Colo. 80123

[21] Appl. No.: 620,864

[22] Filed: Jun. 15, 1984

[51] Int. Cl.⁴ .............................................. G01N 1/12
[52] U.S. Cl. ................... 73/864.63; 73/863.71
[58] Field of Search ........... 73/864.63, 863.71, 864.64, 73/864.65, 864.66, 864.67; 220/208; 294/72, 68.25

[56] References Cited

U.S. PATENT DOCUMENTS

| | | | |
|---|---|---|---|
| 1,585,072 | 5/1926 | Banks | 73/864.63 |
| 2,333,711 | 11/1943 | Dwiggin | 73/864.63 X |
| 3,455,904 | 7/1969 | Hopkin | 73/864.63 X |
| 3,489,012 | 1/1970 | Niskin | 73/864.63 X |
| 3,815,422 | 6/1974 | Niskin | 73/864.67 |
| 3,841,162 | 10/1974 | Duperon | 73/864.67 |
| 4,037,477 | 7/1977 | Niskin | 73/864.67 X |
| 4,050,315 | 9/1977 | Markfelt | 73/864.66 |
| 4,091,676 | 5/1978 | Niskin | 73/864.67 |
| 4,157,664 | 6/1979 | Robinson | 73/864.66 X |
| 4,271,704 | 6/1981 | Peters | 73/864.63 |

FOREIGN PATENT DOCUMENTS

| | | | |
|---|---|---|---|
| 598970 | 6/1934 | Fed. Rep. of Germany | 73/864.65 |
| 1496505 | 12/1977 | United Kingdom | 73/864.63 |
| 188405 | 11/1966 | U.S.S.R. | 73/864.67 |
| 800783 | 2/1981 | U.S.S.R. | 73/864.63 |

Primary Examiner—Stewart J. Levy
Assistant Examiner—Tom Noland
Attorney, Agent, or Firm—Wm. Griffith Edwards

[57] ABSTRACT

A device for collecting samples of water from wells and the like comprises an elongated container having valves at both ends which valves are arranged to open when the container is lowered in a body of water and to close when the container is stopped and to remain closed when the container is being raised to the surface. The device traps a sample of the water at the position at which the device is stopped, and the container is held closed during the entire return to the surface.

9 Claims, 2 Drawing Figures

LIQUID SAMPLE COLLECTOR AND METHOD FOR OBTAINING SAMPLES

This invention relates to an improved device for capturing and retrieving truly representative samples of liquids from wells or other locations below the surface level of the liquid to be sampled.

BACKGROUND OF THE INVENTION

Various devices and methods have been provided heretofore for the purpose of obtaining liquid samples from below the surface of a body of liquid. These devices fall generally in respective ones of five groups.

The devices of the first group employ a container which is lowered into the body of liquid while in its open position and is provided with a trigger for closing the container by spring action, the trigger being actuated by a dropped messenger weight which trips the trigger whereupon the container is closed. Samples taken by these open devices are subject to possible mixing of the well fluids and contamination of the sample on passing through the air-liquid interface.

The devices of the second group employ a bottle-like container provided with a cork-like closure which is extricated by a jerk of the retrieval rope or line. These devices require auxiliary weights to sink them below the air-liquid surface, are limited in capacity and depth capability, and may involve undesired mixing of the fluids in the body of liquid when employed in a well.

The third group includes bailers having a single valve at the bottom of the container which is opened by bumping the bottom of the well. This device is intended primarily for removal of trash from the bottom of a well and is not suitable for the taking of true samples.

The fourth group comprises simple bucket-type devices, open at the top. They require weight to overcome flotation, and involve a mixing of liquids due to passage through the air-liquid interface zone. These devices do not provide depth-of-sample selectivity.

The fifth group includes devices having a chamber closed at the bottom by a control valve and open at the top through a sampling passage and having a freely movable valve member inside the chamber having a specific gravity less than that of the fluid to be sampled. The chamber is charged with gas to a pressure substantially the same as that in the fluid to be sampled at the sampling depth and the free member is held against the sampling passage which is held closed thereby. When the device is lowered in the fluid to be sampled, the passage is opened by release of the member when the pressures in the chamber and in the surrounding fluid are equal. The chamber then fills and is removed with the samples contained therein.

While the devices of these five groups may be suitable and effective for some sampling applications they are not effective for all purposes and, accordingly, it is an object of the present invention to provide an improved fluid sampling device which is effective for taking a truly representative sample of a liquid at a selected location below the surface of a body of the liquid.

It is another object of the present invention to provide an improved device which is effective for securing samples of liquid at selected depths without contamination by fluids or foreign matter present in the liquid through which the device must pass to a selected sampling position.

BRIEF SUMMARY OF THE INVENTION

The device of this invention includes an elongated closed chamber constructed of stainless steel or other suitable material and provided with normally closed valves near its top and bottom ends. When the chamber is lowered through a liquid body the lower valve opens automatically at a predetermined depth, which may be about one-half foot, and liquid then flows through the chamber as it descends, the upper valve opening automatically. The descent of the chamber is stopped at the selected sampling position and both valves close automatically thereby capturing the sample. The valves remain closed while the chamber is being retrieved. The sample is then removed from the retrieved chamber and retained in a suitable receptacle. The liquid removed from the chamber is a true sample of the liquid at the selected sampling position.

DETAILED DESCRIPTION

Figure 1:
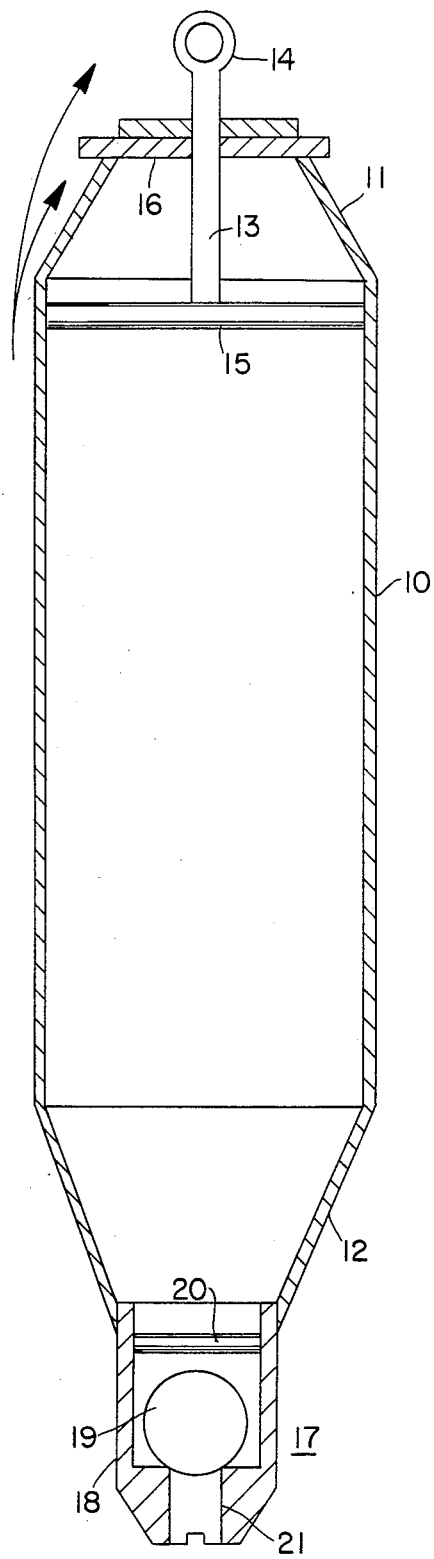
FIG. 1 is a somewhat diagramatic longitudinal section view of a liquid sample collector embodying the invention.

Referring now to the drawing, the liquid sampling device illustrated in FIG. 1 comprises an elongated cylindrical body 10 having a conical top end piece 11 and a conical bottom end piece 12. The pieces 11 and 12 are welded or otherwise suitably secured to the body 10.

The sampling device is arranged to be suspended on a cable or other suitable line and a rod 13 having an attaching ring 14 is provided for this purpose. The rod is secured to a bar or spider 15 which is welded or otherwise securely attached to the inner wall of the body 10. The top valve 16 is a circular plate slidably mounted on the rod 13 for free linear movement toward and away from the top end piece 11 of the body 10. The top edge of the piece 11 and the bottom face of the valve plate 16 are provided with cooperating smooth flat surfaces which engage one another to seal the top opening of the cylinder 10. The diameter of the plate 16 is greater than that of the valve seat on the cone 11 and less than the diameter of the body 10. The density of the valve plate material is greater than the density of the liquid to be sampled. For purposes of assembly and servicing the rod 13 may be secured to the bar by a threaded connection.

The bottom valve assembly, indicated at 17, includes a cylindrical fitting 18 welded or otherwise secured to the bottom of the conical piece 12. A ball valve 19 is retained in the fitting by a bar 20 and is free to move toward and away from the bottom outlet indicated at 21. The diameter of the ball is such that the annular space around the ball has a minimum cross section about the horizontal circumference of the ball which is substantially the same area as that of the outlet 21, and these passages are approximately equivalent in hydraulic characteristics.

The ball 19 is spherical and made of a material having a density selected with respect to the density of the liquid to be sampled so that the valve 19 opens at a predetermined depth below the surface of the body of liquid to be sampled. Thus the valve 19 may be designed to open when the intake 21 is, say, six inches below the surface of the liquid. This avoids the admission of trash, bacterial growth or other contaminating substance which may be present near the surface of the body of liquid. By way of example, a ceramic ball 1.2 inches in diameter was found to be displaced from its seat when at a depth of five inches in a body of water when the collecting chamber was empty. Thus the material of the ball valve may be selected to meet the requirements of a particular application. The fitting 17 may be made readily detachable as by securing it to the body 10 by a threaded connection so that ball valves of different densities may be employed if required for unusual applications.

The material of the device may be stainless steel or other inert material of sufficient strength. This prevents contamination of the samples due, for example, to corrosive substances in some liquids and avoids compromise of the representative nature of the results when the samples are analyzed.

During the operation of the device of this invention the ring 14 is attached to a line and the empty device is lowered into the body of liquid to be analyzed. The valve 19 will open at the depth for which it is designed and liquid will flow into the body 10 displacing air which escapes around the upper valve 16 and, thereafter, as the device descends liquid flows continuously through the body 10. The movement of the device through the body of liquid acts to produce the flow of liquid against the overhanging edge of the plate valve 16 and this aids in keeping the valve open and helping to maintain a free flow of liquid through the device. The downward movement is stopped at the location where a sample is to be taken and both the valves 19 and 16, which are of material of greater density than the liquid, close immediately. As a result the sample is taken of the liquid at the position selected, and the device is retrieved immediately, the valves remaining closed during the upward return movement of the device.

The sample is then removed and transferred to a suitable container for transportation and analysis.

Figure 2:
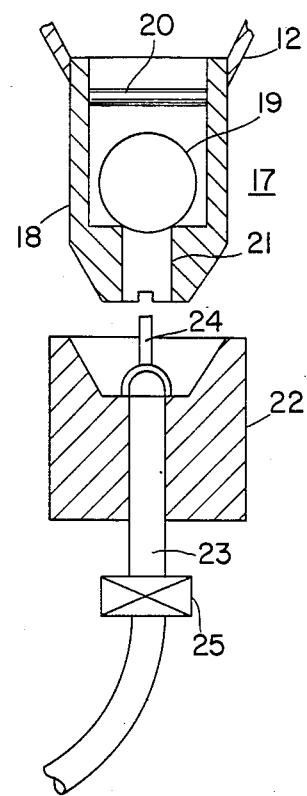
FIG. 2 is a somewhat diagramatic sectional view of a discharge coupling for the collector of FIG. 1.

The coupling illustrated in FIG. 2 is provided to facilitate the transfer of the sample from the device. This coupling includes a block 22 having a central tube 23 of inert material connected thereto, and having a seat for receiving the valve assembly 17. An upwardly extending projection 24 is in the center of the block directly over the tube for engaging and opening the valve. A check valve 25 is provided in the tube 23 to prevent the flow of fluid from the tube to the device. The sample may then be directed through the tube 23 to the desired containers for purposes of analysis. Rapid upward velocity increases the tightness of the valve closure so that the sample may be retrieved intact, uncontaminated and truly representative of the liquid present at the selected sample point.

The device may be provided in a wide range of sizes. Most frequently, the diameter of the body ranges from one inch to four inches and, depending upon the required capacity, the length may range from six inches to five feet. In other applications different sizes may be required and the device is not limited to any fixed range of dimensions.

The performance of the device of this invention has been confirmed by laboratory tests and by field use. The device has been tested and found to be fully effective over a range of water depths from five feet to 1500 feet.

While a particular embodiment of the invention has been described other applications and arrangements will occur to those skilled in the art. Therefore, it is not desired that this invention be limited to the specific construction shown and described and it is intended by the accompanying claims to cover all modifications within the spirit and scope of the invention.

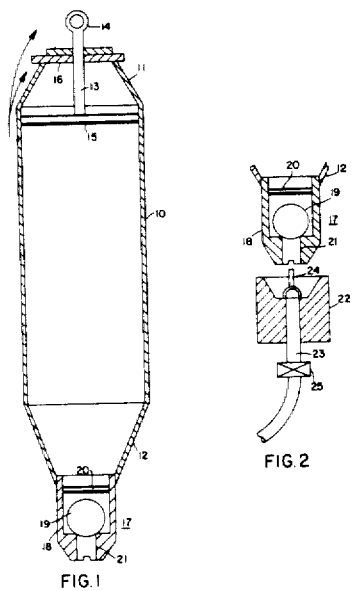

We claim:

1. A liquid sample collecting device comprising: an elongated cylindrical sample collection vessel for use in an upright position and having an upper valve and a lower valve for controlling the movement of liquid upwardly into and through said vessel, said vessel having top and bottom end walls and having its top end wall decreasing in cross section axially from the lowest to the uppermost part thereof and having respective central openings in said end walls for the passage of fluid therethrough under control of said valves, said upper valve including a plate covering the central opening in said top end wall and having a peripheral portion of said plate projecting substantially beyond the outside surface of said top end wall and having its peripheral edge at a distance from the axis of said vessel less than the radius of said vessel, whereby the force of liquid moving over the outer wall of said vessel acts against said peripheral portion and assists the internal pressure in opening said upper valve, means dependent upon the direction of vertical movement of said vessel in a body of liquid to be sampled for opening said valves during downward movement and for closing said valves upon stopping of downward movement and during upward movement, whereby when said vessel is lowered into a body of liquid to a predetermined submerged position said valves are opened during the downward movement and liquid moves through said vessel and on stopping downward movement the valves are closed to trap a sample of the liquid and are maintained closed during upward movement for delivering the sample to the surface.

2. The invention set forth in claim 1 wherein said lower valve is a ball valve and including means for delaying the opening of said lower valve until said vessel has moved a predetermined distance into the body of liquid.

3. The invention set forth in claim 2 wherein said means effective during downward movement utilizes hydrodynamic forces for opening said valves.

4. The invention set forth in claim 2 wherein said lower valve is a ball valve and the ball is constructed of a material having a density greater than that of the liquid of said body and selected to cause the ball valve to open at a short distance below the surface of the body of liquid and below contaminating substances in the liquid.

5. The invention as set forth in claim 4 wherein the material of said ball valve is a ceramic having a density greater than that of the liquid of said body.

6. The invention set forth in claim 1 wherein said means effective during downward movement utilizes hydrodynamic forces for opening said valves.

7. The invention set forth in claim 1 wherein said vessel has a central element secured to its inner wall and extending upwardly for attachment to a supporting line, and said top valve is slidably mounted on said element.

8. The invention set forth in claim 1 wherein the top end of said vessel has a flat surface normal to the longitudinal axis of said vessel and said top valve has a flat surface which engages said flat surface of the vessel in its closed position.

9. The invention set forth in claim 1 wherein said vessel includes a cylindrical fitting secured thereto and extending downwardly therefrom and having an opening constituting said opening in said bottom end wall, and wherein said bottom valve is a ball arranged in said fitting and the annular passage formed thereby in said fitting about said ball has a cross-sectional area the minimum of which is approximately equal to the cross-sectional area of said opening in said bottom end wall, thereby making the bottom end wall opening and the annular passage has approximately equivalent hydraulic characteristics.

* * * * *

UNITED STATES PATENT AND TRADEMARK OFFICE
CERTIFICATE OF CORRECTION

PATENT NO. : 4,590,810  
DATED : May 27, 1986  
INVENTOR(S) : Geoffrey G. Hunkin et al.

Page 1 of 3

It is certified that error appears in the above-identified patent and that said Letters Patent is hereby corrected as shown below:

The title page showing the illustrative figure should be deleted to appear as per attached title page.

Figures 1 and 2 should appear as shown on the attached sheets.

Signed and Sealed this

Twenty-fifth Day of November, 1986

*Attest:*

DONALD J. QUIGG

*Attesting Officer*        *Commissioner of Patents and Trademarks*

United States Patent [19]

Hunkin et al.

[11] Patent Number: 4,590,810
[45] Date of Patent: May 27, 1986

[54] LIQUID SAMPLE COLLECTOR AND METHOD FOR OBTAINING SAMPLES

[76] Inventors: Geoffrey G. Hunkin, 9 Meadow Lark La.; Thomas A. Reed, 6458 S. Garland Ct., both of Littleton, Colo. 80123

[21] Appl. No.: 620,864

[22] Filed: Jun. 15, 1984

[51] Int. Cl.⁴ .............................................. G01N 1/12
[52] U.S. Cl. .............................. 73/864.63; 73/863.71
[58] Field of Search .......... 73/864.63, 863.71, 864.64, 73/864.65, 864.66, 864.67; 220/208; 294/72, 68.25

[56] References Cited

U.S. PATENT DOCUMENTS

| | | | |
|---|---|---|---|
| 1,585,072 | 5/1926 | Banks | 73/864.63 |
| 2,333,711 | 11/1943 | Dwiggin | 73/864.63 X |
| 3,455,904 | 7/1969 | Hopkin | 73/864.63 X |
| 3,489,012 | 1/1970 | Niskin | 73/864.63 X |
| 3,815,422 | 6/1974 | Niskin | 73/864.67 |
| 3,841,162 | 10/1974 | Duperon | 73/864.67 |
| 4,037,477 | 7/1977 | Niskin | 73/864.67 X |
| 4,050,315 | 9/1977 | Markfelt | 73/864.66 |
| 4,091,676 | 5/1978 | Niskin | 73/864.67 |
| 4,157,664 | 6/1979 | Robinson | 73/864.66 X |
| 4,271,704 | 6/1981 | Peters | 73/864.63 |

FOREIGN PATENT DOCUMENTS

| | | | |
|---|---|---|---|
| 598970 | 6/1934 | Fed. Rep. of Germany | 73/864.65 |
| 1496505 | 12/1977 | United Kingdom | 73/864.63 |
| 188405 | 11/1966 | U.S.S.R. | 73/864.67 |
| 800783 | 2/1981 | U.S.S.R. | 73/864.63 |

*Primary Examiner*—Stewart J. Levy
*Assistant Examiner*—Tom Noland
*Attorney, Agent, or Firm*—Wm. Griffith Edwards

[57] ABSTRACT

A device for collecting samples of water from wells and the like comprises an elongated container having valves at both ends which valves are arranged to open when the container is lowered in a body of water and to close when the container is stopped and to remain closed when the container is being raised to the surface. The device traps a sample of the water at the position at which the device is stopped, and the container is held closed during the entire return to the surface.

9 Claims, 2 Drawing Figures

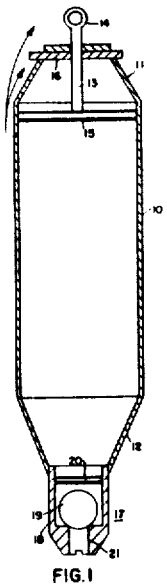

FIG.1

UNITED STATES PATENT AND TRADEMARK OFFICE
CERTIFICATE OF CORRECTION

PATENT NO. : 4,590,810            Page 3 of 3
DATED     : May 27, 1986
INVENTOR(S) : Geoffrey G. Hunkin et al It is certified that error appears in the above-identified patent and that said Letters Patent is hereby corrected as shown below: